ns Patent [19]

United States Patent [19]
Englaender et al.

[11] 4,376,866
[45] Mar. 15, 1983

[54] PROCESS FOR THE PREPARATION OF α-HYDROXYMETHYLENE ARYLACETIC ACID

[75] Inventors: Fritz Englaender, Bonn; Moustafa El-Chahawi, Troisdorf; Wilhelm Vogt, Cologne, all of Fed. Rep. of Germany

[73] Assignee: Dynamit Nobel AG, Troisdorf, Fed. Rep. of Germany

[21] Appl. No.: 343,029

[22] Filed: Jan. 27, 1982

[30] Foreign Application Priority Data

Jan. 31, 1981 [DE] Fed. Rep. of Germany ....... 3103308

[51] Int. Cl.$^3$ .............................................. C07C 69/76
[52] U.S. Cl. ........................................ 560/60; 560/51
[58] Field of Search ................................... 560/60, 51

[56] References Cited

U.S. PATENT DOCUMENTS 3,130,233 4/1964 Niederhauser ...................... 508/428
3,939,184 2/1976 Koenig et al. ......................... 560/60

FOREIGN PATENT DOCUMENTS 168876 7/1934 Switzerland .......................... 560/60

Primary Examiner—Paul J. Killos
Attorney, Agent, or Firm—Felfe & Lynch

[57] ABSTRACT

New process for making esters of α-hydroxymethylene arylacetic acid from the corresponding arylacetic acid ester by conversion with an alkali alcoholate and carbon monoxide. The resulting hydroxy methylene compound can be obtained from the resulting alkali salt by release with an acid.

5 Claims, No Drawings

PROCESS FOR THE PREPARATION OF α-HYDROXYMETHYLENE ARYLACETIC ACID

This invention relates to an improved process for the manufacture of alkyl esters of α-hydroxymethylene arylacetic acid from the corresponding acetic esters, using alkali alcoholate and carbon monoxide under elevated temperature and pressure.

It is known that a solution of the methyl ester of phenylacetic acid, metallic sodium or potassium, and methyl formate in ether will form the sodium salt of the methyl ester of α-hydroxymethylene phenylacetic acid (Wislicenus, *Annalen der Chemie* 282, 231 [1894]). The reaction, however, is incomplete, and separation from the unconverted phenylacetic acid ester difficult.

This known process is not suitable for the technical manufacture of the methyl ester of α-hydroxymethylene phenylacetic acid because it employs metallic sodium.

It has, however, been discovered that high yields of extremely pure alkyl esters of α-hydroxymethylene arylacetic acid can be obtained by converting the alkyl esters of acrylacetic acid with sodium alkoxide and carbon monoxide under increased temperature and presure. In contrast to the hazardous and problematic method employing alkali metals, this process is simple and safe and can be used to obtain yields of up to 95% of the theoretical.

The reaction time for the process in accordance with the invention is approximately 3 hours, whereas converting the esters of formic acid with an alkali metal takes 24 hours.

The object of the invention is therefore a process for manufacturing alkyl esters of α-hydroxymethylene arylacetic acid, characterized by the conversion of arylacetic acid alkyl esters with the general formula $R_1CH_2CO_2R_2$, in which $R_1$ is an aryl residue and $R_2$ a straight-chain or branched alkyl residue, with carbon monoxide in the presence of an alkali alkoxide. The appropriate temperatures range from 30° to 150° C. The carbon monoxide pressures range from 20 to 200 bar. Temperatures of from 40° to 85° C. and pressures of from 80 to 100 bars are preferred.

Conversion and yield are practically quantitative. Especially remarkable is the extreme purity of the product. When conversion is complete, the alkali salt of the alkyl ester of α-hydroxymethylene arylacetic acid will be suspended in the solvent. When this suspension is added to an excess of an aqueous acid, preferably hydrochloric acid or sulfuric acid, the free α-hydroxymethylene compound will form and dissolve in the solvent, while the resulting sodium chloride will separate with the water. The alkyl ester of the α-hydroxymethylene arylacetic acid can be readily obtained from the organic phase by distillation or crystallization.

Suitable solvents are those with boiling points of 35° to 180° C., such as aliphatic and aromatic hydrocarbons like the benzine fractions benzene, toluene, or the xylenes, aliphatic ethers like those with 2 to 6 carbon atoms or like dioxan, or aliphatic alcohols with 1 to 4 carbon atoms.

It is also possible to employ the starting material as a solvent. Preferred solvents are the aromatic hydrocarbons, especially toluene. The type and quantity of solvent should be selected to ensure that no solid precipitates from the product suspension. Aryl acetic esters with alcohol residues $R_2$ that have 1 to 6 carbon atoms, especially the methyl and ethyl esters, are used above all. The aryl residue $R_1$ of the esters can contain one or two aromatic rings, either unsubstituted, containing that is only hydrogen as a substituent, or containing one or more substituents inert to the reaction, especially halogens like chlorine or bromine or lower alkyl residues with 1 to 4 carbon atoms, preferably a methyl or ethyl residue. Substituted or unsubstituted phenyl residues, α- or β-naphthyl residues, or biphenyl residues are preferred.

The alkali alkoxide to be employed is preferably sodium methylate or sodium ethylate. Alkoxides of other aliphatic alcohols with 1 to 6 carbon atoms can also be employed, however. Generally the alkoxide with an alcohol residue that corresponds to that of the ester, sodium methylate with a methyl ester for example, is employed in order to avoid side reactions. To the extent that alcohols are employed as solvents, ethyl alcohol will be used with an ethyl ester as a starting material and methyl alcohol with a methyl ester.

Although the sodium alkoxides are preferred by far, alkoxides of potassium and even lithium can also be employed. The alkoxide can be employed as a solid dissolved in whatever solvent, preferably toluene, is employed or as a solution in the corresponding alcohol.

An excess of alkoxide in relation to the esters is to be preferred in this reaction, except when the ester itself is used as a solvent. The alkoxide excess may range from 0.5 to 20 and preferably from 2.5 to 5 mole percent.

The resulting alkyl esters of α-hydroxymethylene arylacetic acids have a wide range of uses as intermediate products in the manufacture of heterocyclic compounds like the 7-aminocoumarins the manufacture of which is disclosed in Auslegeschrift No. 1 278 444.

EXAMPLE 1

150 parts by weight of the methyl ester of phenylacetic acid, 56.7 parts by weight of sodium ethylate, and 516 parts by weight of toluene were heated to 55° C. under a carbon monoxide pressure of 100 bar. At 45° C., the carbon monoxide began to be absorbed rapidly. Since the carbon monoxide consumed was replaced, the pressure varied between 90 and 100 bar. As soon as the pressure stopped decreasing the batch was cooled and the carbon monoxide pumped off. The suspension was added to 300 parts by weight of a 12.8% aqueous solution by weight of hydrochloric acid and stirred until the sodium salt went into solution. The toluene phase was separated and distilled. The yield was 166 parts by weight (93.3% of the theoretical) of the methyl ester of α-hydroxymethylene phenylacetic acid with a melting point of 41° C. Gas chromatography showed the compound to be 99.9% pure.

EXAMPLE 2

Subject to the same reaction conditions as in Example 1, (a) methyl ester of 4-chlorophenylacetic acid and
(b) methyl ester of 2-chlorophenylacetic acid were converted. Processing resulted in (a) a yield of 88.2% of the methyl ester of α-hydroxymethylene-4-chlorophenylacetic acid and
(b) a yield of 84.8% of the methyl ester of α-hydroxymethylene-2-chlorophenylacetic acid respectively.
Cl calc.: 16.67%

Cl emp.: 16.71% methyl ester of α-hydroxymethylene-4-chlorophenylacetic acid

Cl emp.: 16.83% methyl ester of α-hydroxymethylene-2-chlorophenylacetic acid

EXAMPLE 3

174 Parts by weight of the methyl ester of α-naphthylacetic acid, 48.1 parts by weight of sodium ethylate, and 450 parts by weight of toluene were heated to 80° C. under a carbon monoxide pressure of 100 bar. Since the carbon monoxide consumed was replaced, the pressure varied between 90 and 100 bar. Upon completion of the reaction the batch was cooled and the unreacted carbon monoxide pumped off. The suspension of the sodium salt in toluene was added to 1 l of ice water and, after dissolution of the sodium salt, the toluene phase separated. Acidifying the aqueous phase yielded the (gas chromatographically) 99.5% pure methyl ester of α-hydroxymethylene-α-naphthylacetic acid, which had a melting point of from 124° to 126° C.

|   | calc. | emp. |
|---|---|---|
| C: | 73.67 | 73.92 |
| H: | 5.3 | 5.66 |

It will be understood that the specification and examples are illustrative but not limitative of the present invention and that other embodiments within the spirit and scope of the invention will suggest themselves to those skilled in the art.

What is claimed is:

1. Process for the manufacture of alkyl esters of α-hydroxymethylene arylacetic acids, which comprises reacting the corresponding arylacetic acid alkyl ester, of the formula $R_1CH_2CO_2R_2$, in which $R_1$ is an aryl radical and $R_2$ is straight-chain or branched alkyl, with carbon monoxide in the presence of an alkali alcoholate.

2. Process as claimed in claim 1, wherein the reaction is carried out in the presence of a solvent.

3. Process as claimed in claim 1, wherein the conversion is carried out at temperatures of between 30° and 150° C.

4. Process as claimed in claim 1, wherein the conversion is carried out under pressures of 20 to 200 bar.

5. Process as claimed in claim 1, wherein, after completion of the reaction, the alkyl ester of α-hydroxymethylene arylacetic acid is released from the sodium salt of the alkyl ester of α-hydroxymethylene arylacetic acid with an acid.

* * * * *